(12) United States Patent
Cotty et al.

(10) Patent No.: US 7,879,978 B2
(45) Date of Patent: Feb. 1, 2011

(54) *MACACA FASCICULARIS* ST2L (75) Inventors: Adam Cotty, Radnor, PA (US); Natalie Fursov, Radnor, PA (US); Michael Naso, Radnor, PA (US)

(73) Assignee: Centocor Ortho Biotech, Inc., Horsham, PA (US)

( * ) Notice: Subject to any disclaimer, the term of this patent is extended or adjusted under 35 U.S.C. 154(b) by 11 days.

(21) Appl. No.: 12/415,095

(22) Filed: Mar. 31, 2009

(65) Prior Publication Data

US 2010/0247442 A1    Sep. 30, 2010

(51) Int. Cl.
C07K 14/52 (2006.01)
C07K 14/00 (2006.01)
G01N 33/53 (2006.01)

(52) U.S. Cl. .......... 530/351; 530/350; 436/501

(58) Field of Classification Search .......... None
See application file for complete search history.

(56) References Cited

U.S. PATENT DOCUMENTS 6,323,334 B1 * 11/2001 Kingsbury et al. ......... 536/23.5

OTHER PUBLICATIONS

Tominaga, et al., "A putative protein of a growth specific cDNA from BALB/c-3T3 cells is highly similar to the extracellular portion of mouse interleukin 1 receptor," FEBS Letters, 258(2):301-304 (1989).

Meisel et al., "Regulation and Function of T1/ST2 Expression on CD4 T Cells: Induction of Type 2 Cytokine Production by T1/ST2 Cross-Linking," Journal of Immunology, 166:3143-3150 (2001).

Trajkovic et al., "T1/ST2—an IL-1 receptor-like modulator of immune responses," Cytokine Growth Factor Reviews, 15:87-95 (2004).

Schmitz et al., "IL-33, an Interkeukin-1-like-Cytokine that Signals via the IL-1 Receptor-Related Protein ST2 and Induces T Helper Type 2-Associated Cytokines," Immunity, 23:479-490 (2005).

Kakkar, et al., "The IL-33/ST2 pathway: therapeutic target and novel biomarker," Nature Reviews 7:827-840 (2008).

Coyle et al., "Crucial Role of the Interleukin 1 Receptor Family Member T1/ST2 in T Helper Cell Type 2-mediated Lung Mucosal Immune Responses," Journal of Experimental Medicine, 190:895-902 (1999).

Hayakawa et al., "Soluble ST2 Blocks Interleukin-33 Signaling in Allergic Airway Inflammation," Journal of Biological Chemistry, 282(36):26369-26380 (2007).

Leung et al., "A Novel Therapy of Murine Collagen-Induced Arthritis with Soluble T1/ST2," Journal of Immunology, 173:145-150 (2004).

Shimizu, et al., "Functional SNPs in the distal promoter of the *ST2* gene are associated with atopic dermatitis," Human Molecular Genetics, 14(19):2919-2927 (2005).

GenBank Accession No. NM_016232.4 (1992).

* cited by examiner

*Primary Examiner*—Christine J Saoud
*Assistant Examiner*—Jegatheesan Seharaseyon
(74) *Attorney, Agent, or Firm*—Kirk Baumeister (57) ABSTRACT

Isolated polynucleotides encoding *Macaca fascicularis* ST2L (Cyno ST2L), polypeptides obtainable from expression of these polynucleotides, recombinant cells, and methods of use are disclosed.

5 Claims, 3 Drawing Sheets

Figure 1

| | |
|---|---|
| HsSTL2 | MGFWILAILTILMYSTAAKFSKQSWGLENEALIVRCPRQGKPSYTVDWYYSQTNKSIPTQ |
| CynoST2L | MGLWILAILTILVYSTAAKFSKQSWGLENEALIVRCPRQGKSSYIVDWYYSQTNKSIPTQ |
| | :****.***************************. ************ |
| | |
| HsSTL2 | ERNRVFASGQLLKFLPAAVADSGIYTCIVRSPTFNRTGYANVTIYKKQSDCNVPDYLMYS |
| CynoST2L | ERNRVFASGQLLKFLPAEVADSGIYTCIVRSPTFNRTGYANVTIYKKQPDCNVPDYLMYS |
| | ***************.************************** .******** |
| | |
| HsSTL2 | TVSGSEKNSKIYCPTIDLYNWTAPLEWFKNCQALQGSRYRAHKSFLVIDNVMTEDAGDYT |
| CynoST2L | TVSGSEKNSKIYCPTIDLYNWTAPLEWFKNCQALQGSRYKAHKSFLVIDNVMTDDAGDYT |
| | *************************************:********:**** |
| | |
| HsSTL2 | CKFIHNENGANYSVTATRSFTVKDEQGFSLFPVIGAPAQNEIKEVEIGKNANLTCSACFG |
| CynoST2L | CKFIHNENGANYSVTATRSFTVKDEQGFSLFPVIRAPAHNETKEVEIGENTNLTCSACFG |
| | ******************************** *. ****:*.******** |
| | |
| HsSTL2 | KGTQFLAAVLWQLNGTKITDFGEPRIQQEEGQNQSFSNGLACLDMVLRIADVKEEDLLLQ |
| CynoST2L | KGAQFLATVQWQLNGNKITDFSEPRIQQEEGQNQSFSNGLACVNTVLRIADVKEEDLLLR |
| | :**:* ***.*.****************:: *************: |
| | |
| HsSTL2 | YDCLALNLHGLRRHTVRLSRKNPIDHHSIYCIIAVCSVFLMLINVLVIILKMFWIEATLL |
| CynoST2L | YDCLALNLHGLRRHTIRLSRKNPIDHQSTYCIIAVCSVLLMLINVLVIILKTFWIEATLL |
| | *************:*******.*:*******:*******: ***** |
| | |
| HsSTL2 | WRDIAKPYKTRNDGKLYDAYVVYPRNYKSSTDGASRVEHFVHQILPDVLENKCGYTLCIY |
| CynoST2L | WRDIAKPYKTRNDGKLYDAYVIYPRNYTSSTDGASRVEYFVHQILPDVLENKCGYTLCIY |
| | *******************:*.*****:******************* |
| | |
| HsSTL2 | GRDMLPGEDVVTAVETNIRKSRRHIFILTPQITHNKEFAYEQEVALHCALIQNDAKVILI |
| CynoST2L | GRDMLPGEDVVTAVETNIRKSRRHIFILTPQITHNEEFAYEQEVALHSALIQNDSKVILI |
| | *********************************:*******.***.*** |
| | |
| HsSTL2 | EMEALSELDMLQAEALQDSLQHLMKVQGTIKWREDHIANKRSLNSKFWKHVRYQMPVPSK |
| CynoST2L | EMEALSELDMLQAEALQDSLRHLMEVQGTIKWREDHVANKRSLNSKFWKHVRYQMPVPSK |
| | ******************:*.********:********************* |
| | |
| HsSTL2 | IPRKASSLTPLAAQKQ |
| CynoST2L | MPRKASSLTSLAAQKQ |
| | :******.**** |

MACACA FASCICULARIS ST2L

FIELD OF THE INVENTION

The present invention relates to *Macaca fascicularis* (cynomolgus) ST2L and its uses.

BACKGROUND OF THE INVENTION

ST2L (IL1RL1, DER4, T1, FIT-1) is a member of the Toll-like/IL-1 receptor superfamily. ST2L was identified as an orphan receptor (Tominaga et al., FEBS Lett. 258:301-304, 1989) and a marker of Th2 cells involved in inflammatory processes, especially in the production of Th2-associated cytokines (Meisel et al., J. Immunol. 166:3143-3150; Trajkovic et al., Cytokine Growth Factor Rev. 15:87-95, 2004). The most characterized binding partner of ST2L is IL-33, which binds ST2L in conjunction with the IL-1R accessory protein (Schmitz et al., Immunity 23:479-490, 2005). ST2L signaling complex also includes a soluble receptor, $sST^2$, which is produced by alternative splicing of ST2L, and can act as a negative regulator of ST2L signaling.

ST2L is selectively expressed on Th2 but not Th1 lymphocytes, mast cells, macrophages and eosinophils. ST2L signaling leads to generation of Th2 cytokines (IL-4, IL-5, IL-13), enhancement of Th2 effector functions, and proliferation of Th2 cells (Kakkar and Lee, Nature Reviews 7:827-840, 2008). Inhibition of ST2L activity attenuates Th2-dominated immune responses, such as lung eosinophilia, airway hyperresponsiveness, and arthritis in animal models (Coyle et al., J. Experimental Medicine 190:895-902, 1999; Hayakawa et al., J. Biol. Chem. 282:26369-26380, 2007; Leung et al., J. Immunol. 173:145-150, 2004). Further support for the role of ST2L signaling in human allergic diseases is supported by association of an ST2L promoter polymorphism that enhances ST2 gene expression with increased risk of developing atopic dermatitis (Shimizu et al., Hum. Mol. Genet. 14:2919-2927, 2005), and by IL-33-induced phenotype with production of IL-5 and IL-13, eosinophilia, increased serum IgE and IgA levels, lung epithelial cell hyperplasia and increased mucus production (Schmitz et al., Immunity 23:479-490, 2005). Thus, modulators of ST2L signaling, such as neutralizing anti-ST2L antibodies, may have a therapeutic benefit for Th2-mediated conditions as well as for inflammatory diseases such as asthma, allergy, and atopic dermatitis.

Predictive pharmacokinetic, safety and efficacy studies will be required before any ST2L modulator for human use can be brought to the market place. Such studies will involve both in vitro and in vivo testing in animal models of ST2L-associated pathologies. Lack of cross-reactivity of the modulators with ST2Ls across species can pose a challenge in these studies. Thus, use of, for example, antibody-based ST2L modulators may require evaluation of cross-reactivity of the antibodies between species, generation of surrogate antibodies against a ST2L polypeptide expressed by a particular model animal, as well as significant in vitro characterization of such surrogate antibodies. Evaluation of cross-reactivity, surrogate generation and in vitro characterization will require the use of ST2L polynucleotides and polypeptides from a suitable animal model. Importantly, the identification of suitable animal models for the above-mentioned studies requires the identification of animal species expressing ST2L with high identity and homology to human ST2L.

Thus, a need exists for the identification of polynucleotides encoding ST2L and ST2L polypeptides being expressed in an animal model identified as suitable for the predictive pharmacokinetic, safety and efficacy studies of ST2L modulators. A need also exists for related methods such as methods of expressing such polypeptides and testing the cross-reactivity of ST2L modulators.

SUMMARY OF THE INVENTION

One aspect of the invention is an isolated polynucleotide encoding a polypeptide comprising the amino acid sequence shown in SEQ ID NO: 2, 4, 6, or 8.

Another aspect of the invention is a vector comprising an isolated polynucleotide having the sequence shown in SEQ ID NO: 1, 3, 5, or 7.

Another aspect of the invention is an isolated host cell comprising a vector of the invention.

Another aspect of the invention is an isolated polypeptide comprising a polypeptide having the sequence shown in SEQ ID NO: 2, 4, 6, or 8.

Another aspect of the invention is a method for expressing a polypeptide of the invention.

Another aspect of an invention is an isolated antibody that specifically binds a polypeptide of the invention.

Another aspect of the invention is a method for determining cross-reactivity of a human ST2L modulator with *Macaca fascicularis* ST2L.

Another aspect of the invention is a method of assessing the safety of a ST2L modulator for use in humans.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise. Thus, for example, reference to "a polypeptide" is a reference to one or more polypeptides and includes equivalents thereof known to those skilled in the art.

Unless defined otherwise, all technical and scientific terms used herein have the same meaning as commonly understood by one of ordinary skill in the art to which an invention belongs. Although any compositions and methods similar or equivalent to those described herein can be used in the practice or testing of the invention, exemplary compositions and methods are described herein.

The present invention provides isolated *Macaca fascicularis* (cynomolgus) ST2L (cynoST2L) polynucleotides, vectors comprising these polynucleotides, isolated host cells, polypeptides obtainable from expression of these polynucleotides, methods for expressing the polypeptides of the invention, and methods of using the polynucleotides and polypeptides of the invention.

The compositions and methods of the invention can be used for a variety of specific applications. The polynucleotides and vectors of the invention are useful because they encode *Macaca fascicularis* ST2L (cynoST2L) polypeptides and can be used to express these polypeptides. These cynoST2L polypeptides are, in turn, useful because they can be used to increase or control Th2-mediated immune responses after exposure to IL-33 or other ST2L ligands when they are recombinantly overexpressed or introduced by other means into a host animal or tissue. The full-length cynoST2L polypeptide sequence of the invention (SEQ ID NO: 8) is 93%. identical, and 96% similar to the human ST2L polypeptide (SEQ ID NO: 10), allowing predictive pharmacokinetic, safety and efficacy studies of ST2L therapeutics, and other uses.

Polypeptides comprising the extracellular domain of cynoST2L can also be used as ligand sink-type antagonists that bind available ST2L ligands or ST2L associated proteins necessary for ST2L activation and thus control ST2L activity. CynoST2L polypeptides can also be used to generate therapeutic antibodies for the positive or negative modulation of the activity of cynoST2L or ST2Ls from other sources. CynoST2L polypeptides can also be used in in vitro or in vivo assays to identify other therapeutics such as small molecules, oligonucleotides or peptides capable of modulating the activity of cynoST2L or other ST2Ls. The methods of expression disclosed are useful because these methods permit the expression of cynoST2L peptides. Other methods disclosed are useful for assessing safety and cross-reactivity of a ST2L therapeutic between animal species.

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "complementary sequence" means a second isolated polynucleotide sequence that is antiparallel to a first isolated polynucleotide sequence and that comprises nucleotides complementary to the nucleotides in the first polynucleotide sequence. Typically, such "complementary sequences" are capable of forming a double-stranded polynucleotide molecule such as double-stranded DNA or double-stranded RNA when combined under appropriate conditions with the first isolated polynucleotide sequence.

The term "vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotides comprising a vector may be DNA or RNA molecules or hybrids of these.

The term "expression vector" means a vector that can be utilized in a biological system or a reconstituted biological system to direct the translation of a polypeptide encoded by a polynucleotide sequence present in the expression vector.

The term "polypeptide" means a molecule that comprises at least two amino acid residues linked by a peptide bond to form a polypeptide. Small polypeptides of less than 50 amino acids may be referred to as "peptides". Polypeptides may also be referred as "proteins."

The term "antibody" refers to a molecule specifically binding to an antigen, and includes dimeric, trimeric and multimeric antibodies, and chimeric, humanized and fully human antibodies. Also, an antibody may be a whole antibody or a functional fragment of an antibody molecule, such as a fragment retaining at least its antigen binding function, and include Fab, F(ab'), F(ab')$_2$, scFv, dsFv, and diabodies. For example, antibody fragments may be obtained using proteolytic enzymes (e.g., a whole antibody is digested with papain to produce Fab fragments, and pepsin treatment results in the production of F(ab')$_2$ fragments). Techniques for the preparation and use of the various antibodies are well known in the art (Ausubel, et al., ed., Current Protocols in Molecular Biology, John Wiley & Sons, Inc., NY 1987-2001; Sambrook, et al., Molecular Cloning: A Laboratory Manual, 2$^{nd}$ Edition, Cold Spring Harbor, N.Y., 1989; Harlow and Lane, Antibodies, a Laboratory Manual, Cold Spring Harbor, N.Y., 1989; Colligan, et al., ed., Current Protocols in Immunology, John Wiley & Sons, Inc., NY 1994-2001; Colligan et al., Current Protocols in Protein Science, John Wiley & Sons, NY, N.Y., 1997-2001; Kohler et al., Nature 256:495-497, 1975; U.S. Pat. No. 4,816,567, Queen et al., Proc. Natl. Acad. Sci. 86:10029-10033, 1989). For example, fully human monoclonal antibodies lacking any non-human sequences can be prepared from human immunoglobulin transgenic mice or from phage display libraries (Lonberg et al., Nature 368:856-859, 1994; Fishwild et al., Nature Biotech. 14:845-851, 1996; Mendez et al., Nature Genetics 15:146-156, 1997; Knappik et al., J. Mol. Biol. 296:57-86, 2000; Krebs et al., J. Immunol. Meth. 265:67-84, 2001).

An antibody molecule or preparation "specifically binds" a given antigen when it binds this antigen with higher affinity and in a specific, as opposed to non-specific fashion, relative to a second non-identical antigen. Stated differently, the "specific binding" of an antibody molecule or preparation can be used to distinguish between two different polypeptides.

The term "deleterious symptom" means any symptom presented by an animal that indicates harm to the animal has occurred.

The term "cross-reactivity" means binding of a second antigen to an antibody that was generated against the first antigen. Cross-reactivity usually occurs between antigen polypeptides of different species, or between polypeptides belonging to a protein family. Exemplary cross-reactivity can be the binding of an antibody generated against human ST2L to a cynoST2L polypeptide.

The term "modulator" means a molecule or preparation that is believed to provide a therapeutic benefit in humans or other animals and is believed to provide that therapeutic benefit, in part, through activating or suppressing ST2L. Such modulators may comprise the polypeptides of the invention. Examples of ST2L therapeutics include ST2L ligands, anti-ST2L antibodies, antibody fragments, peptides, polypeptides, oligonucleotides, low molecular weight chemical compounds and the like. Known ST2L modulators are for example IL-33 (Schmitz et al., Immunity 23:479-490, 2005). Assays for modulators include applying putative modulator compounds to a cell expressing ST2L and then determining the functional effects on ST2L signaling, as described below.

As used herein, the term "modulation of ST2L activity" means partially or completely inhibiting, activating, or enhancing activation of ST2L. Methods of measuring ST2L activity and an effect of a molecule, for example ST2L therapeutic or antibody on ST2L activity may be evaluated using any suitable technique known in the art. An exemplary ST2L activity assay uses a reporter gene assay for ST2L based on NF-κB activation induced by IL-33 ((Schmitz et al., Immunity 23:479-490, 2005). ST2L activity can also be monitored by assessing the amount of cytokines and chemokines, for example IL-4, IL-5, IL-13, produced upon induction of ST2L with IL-33. Secreted molecules can be assayed using enzyme-linked immunosorbent assay (ELISA) or bioassays. These and other suitable readout systems are well known in the art and are commercially available.

One aspect of the invention is an isolated polynucleotide comprising a polynucleotide having the sequence shown in SEQ ID NO: 1 or a complementary sequence thereof. The polynucleotide sequence shown in SEQ ID NO: 1 encodes a polypeptide comprising the predicted mature form of the extracellular domain of cynoST2L.

Another aspect of the invention is an isolated polynucleotide comprising a polynucleotide having the sequence shown in SEQ ID NO: 3 or a complementary sequence thereof. The polynucleotide sequence shown in SEQ ID NO: 3 encodes a polypeptide comprising the predicted cynoST2L signal sequence and the extracellular domain.

Another aspect of the invention is an isolated polynucleotide comprising a polynucleotide having the sequence shown in SEQ ID NO: 5 or a complementary sequence thereof. The polynucleotide sequence shown in SEQ ID NO: 5 encodes a polypeptide comprising the predicted mature form of the cynoST2L extracellular domain, the transmembrane domain, and the cytoplasmic domain.

Another aspect of the invention is an isolated polynucleotide comprising a polynucleotide having the sequence shown in SEQ ID NO: 7 or a complementary sequence thereof. The polynucleotide sequence shown in SEQ ID NO: 7 encodes a polypeptide comprising the predicted cynoST2L signal peptide, the extracellular domain, the transmembrane domain, and the cytoplasmic domain.

The polynucleotides of the invention may be produced by chemical synthesis such as solid phase polynucleotide synthesis on an automated polynucleotide synthesizer. Alternatively, the polynucleotides of the invention may be produced by other techniques such a PCR based duplication, vector based duplication, or restriction enzyme based DNA manipulation techniques. Techniques for producing or obtaining polynucleotides of a given known sequence are well known in the art.

The polynucleotides of the invention may also comprise at least one non-coding sequence, such as transcribed but not translated sequences, termination signals, ribosome binding sites, mRNA stabilizing sequences, introns and polyadenylation signals. The polynucleotide sequences may also comprise additional sequences encoding additional amino acids. These additional polynucleotide sequences may, for example, encode a marker or tag sequence such as a hexa-histidine peptide (Gentz et al., Proc. Natl. Acad. Sci. (USA) 86:821-284, 1989) or the HA peptide tag (Wilson et al., Cell 37:767-778, 1984) which facilitate the purification of fused polypeptides.

Another embodiment of the invention is a vector comprising an isolated polynucleotide having a sequence shown in SEQ ID NO: 1, 3, 5, or 7. The vectors of the invention are useful for maintaining polynucleotides, duplicating polynucleotides, or driving expression of a polypeptide encoded by a vector of the invention in a biological systems, including reconstituted biological systems. Vectors may be chromosomal-, episomal- and virus-derived such as vectors derived from bacterial plasmids, bacteriophages, transposons, yeast episomes, insertion elements, yeast chromosomal elements, baculoviruses, papova viruses such as SV40, vaccinia viruses, adenoviruses, fowl pox viruses, pseudorabies viruses, picornaviruses and retroviruses and vectors derived from combinations thereof, such as cosmids and phagemids.

The vectors of the invention can be formulated in microparticles, with adjuvants, lipid, buffer or other excipients as appropriate for a particular application.

In one embodiment of the invention the vector is an expression vector. Expression vectors typically comprise nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art. Nucleic acid sequence elements and parent vector sequences suitable for use in the expression of encoded polypeptides are also well known in the art. An exemplary plasmid-derived expression vector useful for expression of the polypeptides of the invention comprises an E. coli origin of replication, an aph(3')-1a kanamycin resistance gene, HCMV immediate early promoter with intron A, a synthetic polyA sequence and a bovine growth hormone terminator. Another exemplary plasmid derived expression vector comprises an E. coli origin of replication, an ant(4')-1a kanamycin resistance gene, Rous sarcoma virus long terminal repeat sequences, HCMV immediate early promoter and an SV40 late polyA sequence.

Another embodiment of the invention is an isolated host cell comprising a vector of the invention. Representative host cell examples include Archaea cells; bacterial cells such as Streptococci, Staphylococci, Enterococci, E. coli, Streptomyces, cyanobacteria, B. subtilis and S. aureus; fungal cells such as Kluveromyces, Saccharomyces, Basidomycete, Candida albicans or Aspergillus; insect cells such as Drosophila S2 and Spodoptera Sf9; animal cells such as CHO, COS, HeLa, C127, 3T3, BHK, 293, CV-1, Bowes melanoma and myeloma; and plant cells, such as gymnosperm or angiosperm cells. The host cells in the methods of the invention may be provided as individual cells, or populations of cells. Populations of cells may comprise an isolated or cultured population of cells or cells present in a matrix such as a tissue.

Introduction of a polynucleotide, such as a vector, into a host cell can be effected by methods well known to those skilled in the art (Davis et al., Basic Methods in Molecular Biology, $2^{nd}$ ed., Appleton & Lange, Norwalk, Conn., 1994; Sambrook et al., Molecular Cloning: A Laboratory Manual, $3^{rd}$ ed., Cold Spring Harbor Laboratory Press, Cold Spring Harbor, N.Y., 2001). These methods include calcium phosphate transfection, DEAE-Dextran mediated transfection, microinjection, cationic lipid-mediated transfection, electroporation, transduction, scrape loading, ballistic introduction and infection.

Another aspect of the invention is an isolated polypeptide comprising a polypeptide having the sequence shown in SEQ ID NO: 2. SEQ ID NO: 2 is a polypeptide comprising the predicted mature form of the cynoST2L extracellular domain.

Another aspect of the invention is an isolated polypeptide comprising a polypeptide having the sequence shown in SEQ ID NO: 4. SEQ ID NO: 4 is a polypeptide comprising the predicted cynoST2L signal peptide and the extracellular domain.

Another aspect of the invention is an isolated polypeptide comprising a polypeptide having the sequence shown in SEQ ID NO: 6. SEQ ID NO: 6 is a polypeptide comprising the predicted mature form of the cynoST2L extracellular domain, the transmembrane domain, and the cytoplasmic domain.

Another aspect of the invention is an isolated polypeptide comprising a polypeptide having the sequence shown in SEQ ID NO: 8. SEQ ID NO: 8 is a polypeptide comprising the predicted cynoST2L signal peptide, the extracellular domain, the transmembrane domain, and the cytoplasmic domain.

The polypeptides of the invention may be produced by chemical synthesis, such as solid phase peptide synthesis, on an automated peptide synthesizer. Alternatively, the polypeptides of the invention can be obtained from polynucleotides encoding these polypeptides by the use of cell-free expression systems such as reticulocyte lysate based expression systems, wheat germ extract based expression systems, and *Escherichia coli* extract based expression systems. The polypeptides of the invention can also be obtained by expression and isolation from cells harboring a nucleic acid sequence of the invention by techniques well known in the art, such as recombinant expression of easily isolated affinity labeled polypeptides. Those skilled in the art will recognize other techniques for obtaining the polypeptides of the invention.

The polypeptides of the invention may comprise fusion polypeptides comprising a polypeptide of the invention fused with a second polypeptide. Such second polypeptides may be leader or secretory signal sequences, a pre- or pro- or prepro-protein sequence, as well as naturally occurring, or partially synthetic sequences derived in part from a naturally occurring sequence or an entirely synthetic sequence. Secretory signal or leader polypeptide sequences may be selected to direct secretion of the polypeptides of the invention into the lumen of the endoplasmic reticulum or extracellular environment; such polypeptide sequences may be heterologous or endogenous to any polypeptide from a *Macaca fascicularis* monkey or comprise hybrids of these. Exemplary fusion proteins can be formed by conjugating together a cynoST2L polypeptide having an amino acid sequence shown in SEQ ID NO: 2, 4, 6, or 8, and an alternative scaffold such as designed ankyrin repeat protein (DARPins) (Stumpp and Amstutz, Curr. Opin. Drug Discov. Devel. 10:153-159, 2007), or MIMETIBODY™ construct (Picha et al. Diabetes 57:1926-1934, 2008). Fusion proteins may generally be generated using either recombinant nucleic acid methods or by chemical synthesis methods well known in the art. A MIMETIBODY™ construct has the generic formula (I):

$$(Bp\text{-}Lk\text{-}(V2)_y\text{—}Hg\text{—}C_H2\text{-}C_H3)_{(t)}, \quad (I)$$

where Bp is a peptide or polypeptide capable of binding a molecule of interest, Lk is a polypeptide or chemical linkage, V2 is a portion of a C-terminus of an immunoglobulin variable region, Hg is at least a portion of an immunoglobulin variable hinge region, $C_H2$ is an immunoglobulin heavy chain $C_H2$ constant region and $C_H3$ is an immunoglobulin heavy chain $C_H3$ constant region, y is 0 or 1, and t is independently an integer of 1 to 10.

It is possible to modify the structure of the polypeptides or fragments of the invention for such purposes as enhancing substrate specificity, stability, solubility, and the like. For example, a modified polypeptide can be produced in which the amino acid sequence has been altered, such as by amino acid substitution, deletion, or addition. It is contemplated that an isolated replacement of a leucine with an isoleucine or valine, an aspartate with a glutamate, a threonine with a serine, or a similar replacement of an amino acid with a structurally related amino acid (i.e., conservative mutations) will, in some instances but not all, not have a major effect on the biological activity of the resulting molecule. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981). Whether a change in the amino acid sequence of a polypeptide or fragment thereof results in a functional homolog can be readily determined by assessing the ability of the modified polypeptide or fragment to produce a response in a fashion similar to the unmodified polypeptide or fragment using the assays described herein. Peptides, polypeptides or proteins in which more than one replacement has taken place can readily be tested in the same manner.

The polypeptides of the invention can also be formulated in a pharmaceutically acceptable carrier or diluent. A variety of aqueous carriers may be employed, e.g., 0.4% saline, 0.3% glycine and the like. These solutions are sterile and generally free of particulate matter. These solutions may be sterilized by conventional, well-known sterilization techniques (e.g., filtration). The compositions may contain pharmaceutically acceptable auxiliary substances as required to approximate physiological conditions, such as pH adjusting and buffering agents. The concentration of the polypeptides of the invention in such pharmaceutical formulation can vary widely, i.e., from less than about 0.5%, usually at or at least about 1% to as much as 15 or 20% by weight and will be selected primarily based on fluid volumes, viscosities and other factors, according to the particular mode of administration selected.

The polypeptides and nucleic acids of the invention can also be provided in the form of a pharmaceutical preparation, such as a vaccine for eliciting an immune response, that can be provided in unit dose forms. The appropriate therapeutically effective dose can be determined readily by those of skill in the art. A determined dose may, if necessary, be repeated at appropriate time intervals selected as appropriate by a physician or other person skilled in the relevant art (e.g. nurse, veterinarian, or veterinary technician) during the treatment period.

The polypeptides of the invention can be lyophilized for storage and reconstituted in a suitable carrier prior to use. This technique has been shown to be effective with conventional protein preparations. Lyophilization and reconstitution techniques are well known in the art.

Another embodiment of the invention is a method for expressing a polypeptide comprising the steps of providing a host cell of the invention; culturing the host cell under conditions sufficient for the expression of at least one polypeptide comprising the sequence shown in SEQ ID NO: 2, SEQ ID NO: 4, SEQ ID NO: 6 or SEQ ID NO: 8; and optionally confirming expression of at least one polypeptide comprising the sequence shown in SEQ ID NO: 2, SEQ ID NO: 4, SEQ ID NO: 6 or SEQ ID NO: 8.

Host cells can be cultured under any conditions suitable for maintaining or propagating a given type of host cell and sufficient for expressing a polypeptide. Culture conditions, media, and related methods sufficient for the expression of polypeptides are well known in the art. For example, many mammalian cell types can be aerobically cultured at 37° C. using appropriately buffered DMEM media while bacterial, yeast and other cell types may be cultured at 37° C. under appropriate atmospheric conditions in LB media.

In the methods of the invention the expression of a polypeptide can be confirmed using a variety of different techniques well known in the art. For example, expression of a polypeptide can be confirmed using detection reagents, such as antibodies or receptor ligands specific for an expressed polypeptide, using for example FACS or immunofluorescent techniques. Antibodies that specifically bind to or cross-react with the cynoST2L polypeptides of the invention are one example of such reagents.

Another embodiment of the invention is a polypeptide produced by the methods of invention. Such polypeptides may comprise post-translational modifications including glycosylation or phosphorylation for example. Such polypeptides may also comprise alternative polypeptide forms such as splice variants, truncated forms, or proteolytically modified forms.

Another embodiment of the invention is an antibody that specifically binds a polypeptide of the invention. The polypeptides of the invention can be used to produce polyclonal or monoclonal antibodies against cynoST2L. Techniques for making murine, chimeric, humanized and fully human monoclonal antibodies using protein or nucleic acid immunization are routine and well known to those skilled in the art. Additional discussion and description of such techniques can be found above.

Another embodiment of the invention is a method of determining cross-reactivity of a ST2L modulator with *Macaca fascicularis* ST2L. Even if the polypeptides and epitopes are preserved across species and in the species under consideration for a predictive model for a modulator, cross-reactivity of a modulator should be established before additional experimentation is performed (Loisel et al., Crit. Rev. in Onc. Hematol. 62:34-42, 2007). Cross-reactivity of modulators, antibodies of the invention and other ST2L antibodies to polypeptides and other antigens may be assayed using, for example, competitive and non-competitive assay systems using techniques such as BIAcore analysis, FACS analysis, immunofluorescence, immunocytochemistry, radioimmunoassays, ELISA, "sandwich" immunoassays, immunoprecipitation assays, western blots, immunoradiometric assays, fluorescent immunoassays, and protein A immunoassays. Such assays are routine and well known in the art (Ausubel et al., eds, 1994, Current Protocols in Molecular Biology, Vol. 1, John Wiley & Sons, Inc., New York). Cross-reactivity can also be evaluated by assaying for a biological activity associated with activation of ST2L. Additional discussion of such assays can be found above. For example, cross-reactivity of a human anti-ST2L antibody modulator with cynoST2L polypeptide can be evaluated using an assay assessing effect of the antibody on blocking activation of IL-33-induced NF-κB activation downstream of ST2L.

Another embodiment of the invention is a method for determining if a ST2L modulator is likely to be safe or unsafe for use in humans comprising providing a ST2L modulator, a first *Macaca fascicularis* monkey, and a second *Macaca fascicularis* monkey; administering the ST2L modulator to the first *Macaca fascicularis* monkey; and determining whether the first *Macaca fascicularis* monkey is presenting a deleterious symptom relative to the second monkey, where presentation of a deleterious symptom by the first *Macaca fascicularis* monkey shows the ST2L modulator is potentially unsafe for use in humans and a lack of presentation of a deleterious symptom by the first *Macaca fascicularis* monkey shows the ST2L therapeutic is potentially safe in humans.

In the methods of the invention the determination of whether the first *Macaca fascicularis* monkey is presenting a deleterious symptom relative to the second *Macaca fascicularis* monkey is readily accomplished. For example, a person of ordinary skill in the art such as a veterinarian, veterinarian's assistant, animal technician, or research scientist can determine if a symptom presented by an animal is deleterious. Examples of deleterious symptoms include death, coma, seizures, fever, organ failure, tissue abnormalities, impaired organ function, impaired tissue function, cancers, tumors, ulcers, bleeding, infections and the like. The ST2L modulators that can be tested include an antibody, an antibody portion or fragment, a peptide, a polypeptide, an oligonucleotide, a small molecule, or a combination thereof.

The present invention will now be described with reference to the following specific, non-limiting examples.

Example 1

Isolation of Polynucleotides Encoding *Macaca Fascicularis* ST2L (CynoST2L)

Untranslated Region (UTR) primers for the 5' and 3' ends were designed based on the human ST2L sequence (NCBI accession number NM_016232). PCR was performed using the designed primers (5'cynoST2L UTR1 5'-agatataggc-tactcttcccaac-3' (SEQ ID NO: 11) and 3'cynoST2L UTR2 5'-ctcctcacacttcagtgcagg-3' (SEQ ID NO: 12)) and *Cynomolgus fascicularis* normal pancreas cDNA from BioChain #C1534188-Cy as template. The PCR reaction was run on a 1% agarose TBE gel and a band near the expected size of 1.9 kB was gel extracted using Qiagen Qiaquick Gel Extraction kit #28706. The product was subcloned using the pCR4 TOPO TA kit from Invitrogen #K4575-01 and transformed into TOP10 One Shot chemically competent cells from Invitrogen #C4040-10. The next day colonies were screened using T3 (5'-aattaaccctcactaaaggg-3', SEQ ID NO: 13) and T7 (5'-taatacgactcactataggg-3', SEQ ID NO: 14) primers.

Figure 1:
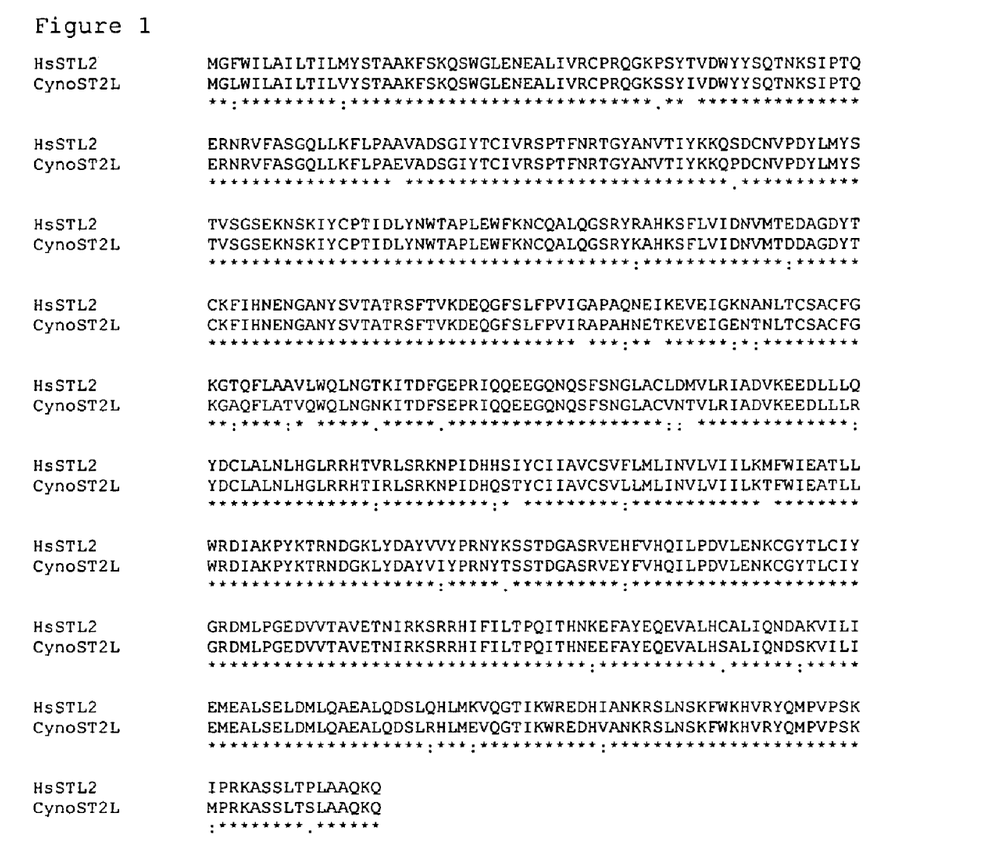
FIG. 1. Protein sequence alignment of cynomolgus vs. human ST2L.

Colonies producing positive bands were then grown up over night in LB media containing 100 ug/ml ampicillin. DNA was isolated using the Qiagen Qiaprep spin mini-kit #27106. The obtained clones were sequenced and the reactions run on the ABI 3100 sequencer. Sequence analysis was performed using Contig Express from the Vector NTI Suite 9 software package. The cloned cynoST2L cDNA was 1671 nucleotides long and encoded a predicted protein of 556 amino acids long. The similarity and identity between the cynoST2L and human ST2L proteins was 93% and 96%, respectively. The alignment between human and cyno ST2L polypeptide sequences is shown in FIG. 1.

Example 2

CynoST2L cDNA Encodes a Functional Protein

In order to assess functionality of the cynoST2L, the ability of cynoST2L to activate downstream signaling pathways was assessed. CynoST2L activated NF-κB upon induction with IL-33. Furthermore, cynoST2L was identified expressed on cell surface using FACS assays.

cDNA encoding full length CynoST2L was cloned into pCR4 TOPO-TA (Invitrogen) into a NotI/BamHI site using primers 5-gtagcagcggccgccaccatggggctttggatcttag-3 (SEQ ID NO: 15) and 5-tgctacggatccctactgcttctgggctgc-3 (SEQ ID NO: 16) using standard techniques. The obtained plasmid DNA was purified and sequenced to confirm correct cloning of the cynoST2L.

HEK293 cells were cultured in DMEM supplemented with 10% FBS. For the reporter gene assays, cells were transfected in 96-well plates. On the day before transfections cells were trypsinized and seeded at 50,000 cells per well in 96-well plate in 50 µl of growth medium. 24 hours after plating, the cells were transfected with DNA according to Lipofectamine 2000 transfection protocol (Invitrogen) using 200 ng of total DNA was transfected per well on 96-well plate. For one well transfection, 4 ng of plasmid encoding the cynoST2L cDNA, 63 ng pBETH vector and 133 ng luciferase plasmid were used. For transfections in flasks, cells were trypsinized and 5 million cells were seeded in 20 ml of growth medium in a T75 flask. The day after plating, 7.5 μg of plasmid encoding the cynoST2L cDNA was mixed with 45 μl Lipofectamine 2000 in 1 ml of OptiMEM medium, incubated for 20 min and added to the cells in T75 flask.

Figure 2:
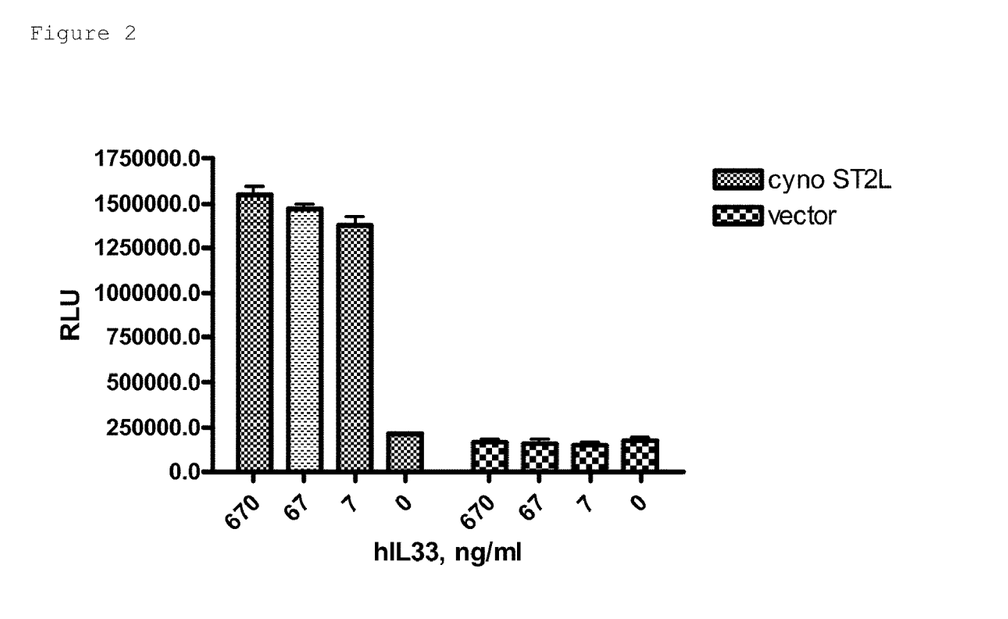
FIG. 2. Human IL33-induced activation of cynoST2L.

Reporter gene assay. 24 hours after transfection the cells were treated with recombinant human IL-33, R&D systems cat#3625-IL/CF. 16 hours after treatment cells were lysed and luciferase activity was measured according to the assay manufacturer protocol (Promega #E2510). Results of the reporter gene assay are shown in FIG. 2.

Figure 3:
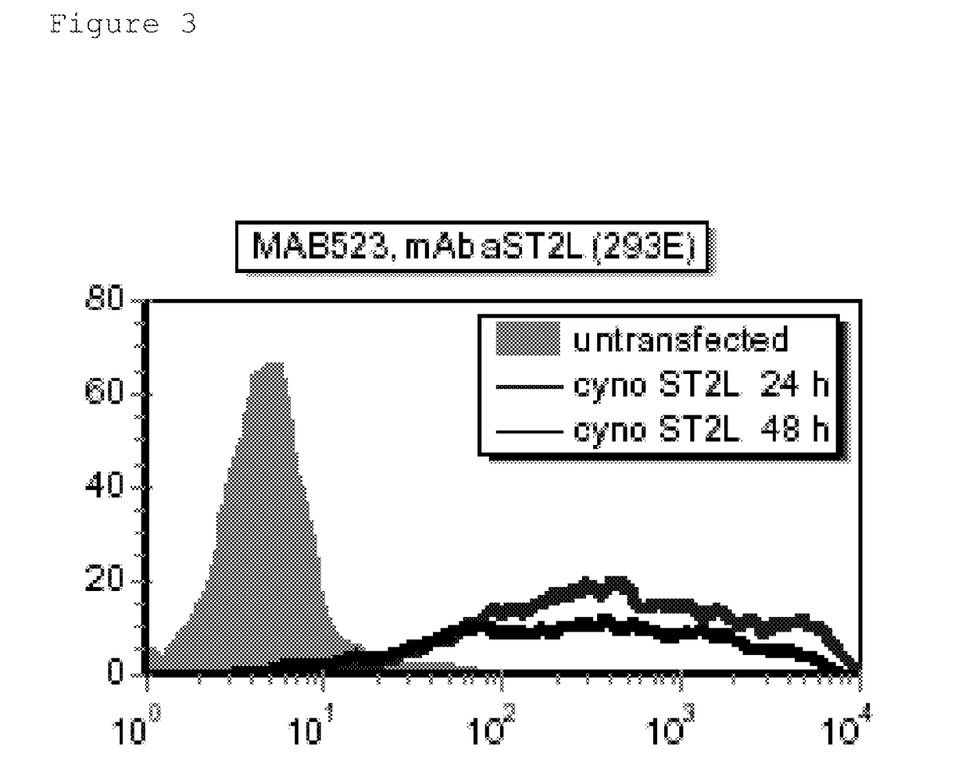
FIG. 3. Cell surface expression of cynoST2L.

FACS assay. For the cynoST2L expression analysis, cells were transiently transfected with the receptor in T75 flask as described in the materials and methods. 24 or 48 hours after transfections cynoST2L expression was measured by flow cytometry. In brief, transfected and untransfected control cells were stained with 10 ug/ml of biotinylated anti-human ST2 antibody (R&D systems cat# MAB523) for 30 min in staining buffer (PBS, 5% FCS. 0.0001% EDTA, 0.5% sodium azide) at room temperature. The cells were washed twice with PBS, 0.1% BSA. The secondary staining was done with PE-conjugated anti-mouse IgG, for 30 min in staining buffer at room temperature. The cells were washed twice and analyzed by flow cytometry with FACSCalbur (Beckman-Dickinson). Results of the FACS assay are shown in FIG. 3.

The present invention now being fully described, it will be apparent to one of ordinary skill in the art that many changes and modifications can be made thereto without departing from the spirit or scope of the appended claims.

The invention claimed is:

1. An isolated polypeptide comprising a polypeptide having the sequence shown in SEQ ID NO: 2.
2. An isolated polypeptide comprising a polypeptide having the sequence shown in SEQ ID NO: 4.
3. An isolated polypeptide comprising a polypeptide having the sequence shown in SEQ ID NO: 6.
4. An isolated polypeptide comprising a polypeptide having the sequence shown in SEQ ID NO: 8.
5. A method for determining cross-reactivity of a human ST2L modulator with *Macaca fascicularis* ST2L comprising:

a. providing a ST2L modulator and a *Macaca fascicularis* ST2L isolated polypeptide comprising the sequence shown in SEQ ID NO: 2, SEQ ID NO: 4, SEQ ID NO: 6, or SEQ ID NO: 8;

b. contacting the ST2L modulator with the *Macaca fascicularis* ST2L isolated polypeptide; and c. determining whether the ST2L modulator binds to the *Macaca fascicularis* ST2L isolated polypeptide.

* * * * *

SEQUENCE LISTING

```
<160> NUMBER OF SEQ ID NOS: 16

<210> SEQ ID NO 1
<211> LENGTH: 930
<212> TYPE: DNA
<213> ORGANISM: Macaca fascicularis

<400> SEQUENCE: 1
aagtttagta acaatcgtg gggcctggaa aatgaggctt taattgtgag atgtcctaga      60
caaggaaaat ctagttacat cgtggattgg tattactcac aaacaaacaa aagtattccc     120
acccaggaaa gaaatcgtgt gtttgcctca ggccaacttc ttaagtttct accagctgaa     180
gttgctgatt ctggtattta tacctgcatt gtcagaagtc ccacattcaa taggactgga     240
tatgcgaatg tcaccatata taaaaaacaa ccagattgca acgttccaga ttatttgatg     300
tattcaaccg tatctggatc agaaaaaaat tccaaaattt actgtcctac aattgacctc     360
tacaattgga cagcacctct tgagtggttt aagaattgtc aggctcttca aggatcaagg     420
tacaaggcgc acaagtcatt tttggtcatt gataatgtga tgactgatga tgcaggtgat     480
tatacctgta aatttataca caatgaaaat ggagccaatt atagtgtgac agcgaccagg     540
tccttcacgg tcaaggatga gcaaggcttc tctctgtttc ctgtaatcag agcccctgca     600
cacaatgaaa caaggaagt ggaaattgga gaaaacacaa acctaacttg ctctgcttgt     660
tttggaaaag gcgctcagtt cttggccacc gtccagtggc agcttaatgg aaacaaaatt     720
acagacttca gtgaaccaag aattcaacaa gaggaagggc aaaatcaaag tttcagcaat     780
gggctggctt gtgtaaacac ggttttaaga atagctgatg taaaggaaga ggatttattg     840
ctgcggtacg actgtctggc cctgaatttg catggcttga gaaggcacac cataagacta     900
agtaggaaaa atccaattga tcatcaaagc                                    930

<210> SEQ ID NO 2
<211> LENGTH: 310
<212> TYPE: PRT
<213> ORGANISM: Macaca fascicularis

<400> SEQUENCE: 2

Lys Phe Ser Lys Gln Ser Trp Gly Leu Glu Asn Glu Ala Leu Ile Val
1               5                   10                  15

Arg Cys Pro Arg Gln Gly Lys Ser Ser Tyr Ile Val Asp Trp Tyr Tyr
            20                  25                  30
```

```
Ser Gln Thr Asn Lys Ser Ile Pro Thr Gln Glu Arg Asn Arg Val Phe
        35                  40                  45
Ala Ser Gly Gln Leu Leu Lys Phe Leu Pro Ala Glu Val Ala Asp Ser
    50                  55                  60
Gly Ile Tyr Thr Cys Ile Val Arg Ser Pro Thr Phe Asn Arg Thr Gly
65                  70                  75                  80
Tyr Ala Asn Val Thr Ile Tyr Lys Lys Gln Pro Asp Cys Asn Val Pro
                85                  90                  95
Asp Tyr Leu Met Tyr Ser Thr Val Ser Gly Ser Glu Lys Asn Ser Lys
            100                 105                 110
Ile Tyr Cys Pro Thr Ile Asp Leu Tyr Asn Trp Thr Ala Pro Leu Glu
        115                 120                 125
Trp Phe Lys Asn Cys Gln Ala Leu Gln Gly Ser Arg Tyr Lys Ala His
    130                 135                 140
Lys Ser Phe Leu Val Ile Asp Asn Val Met Thr Asp Ala Gly Asp
145                 150                 155                 160
Tyr Thr Cys Lys Phe Ile His Asn Glu Asn Gly Ala Asn Tyr Ser Val
                165                 170                 175
Thr Ala Thr Arg Ser Phe Thr Val Lys Asp Glu Gln Gly Phe Ser Leu
            180                 185                 190
Phe Pro Val Ile Arg Ala Pro Ala His Asn Glu Thr Lys Glu Val Glu
        195                 200                 205
Ile Gly Glu Asn Thr Asn Leu Thr Cys Ser Ala Cys Phe Gly Lys Gly
    210                 215                 220
Ala Gln Phe Leu Ala Thr Val Gln Trp Gln Leu Asn Gly Asn Lys Ile
225                 230                 235                 240
Thr Asp Phe Ser Glu Pro Arg Ile Gln Gln Glu Glu Gly Gln Asn Gln
                245                 250                 255
Ser Phe Ser Asn Gly Leu Ala Cys Val Asn Thr Val Leu Arg Ile Ala
            260                 265                 270
Asp Val Lys Glu Glu Asp Leu Leu Leu Arg Tyr Asp Cys Leu Ala Leu
        275                 280                 285
Asn Leu His Gly Leu Arg Arg His Thr Ile Arg Leu Ser Arg Lys Asn
    290                 295                 300
Pro Ile Asp His Gln Ser
305                 310

<210> SEQ ID NO 3
<211> LENGTH: 984
<212> TYPE: DNA
<213> ORGANISM: Macaca fascicularis

<400> SEQUENCE: 3
atggggcttt ggatcttagc aattctcaca attctcgtgt attccacagc agcgaagttt      60
agtaaacaat cgtggggcct ggaaaatgag gctttaattg tgagatgtcc tagacaagga     120
aaatctagtt acatcgtgga ttggtattac tcacaaacaa acaaagtat ccccacccag      180 gaaagaaatc gtgtgtttgc ctcaggccaa cttcttaagt ttctaccagc tgaagttgct     240
gattctggta tttatacctg cattgtcaga agtcccacat caataggac tggatatgcg      300 aatgtcacca tatataaaaa acaaccagat gcaacgttc cagattattt gatgtattca      360
accgtatctg gatcagaaaa aaattccaaa atttactgtc ctacaattga cctctacaat     420
tggacagcac ctcttgagtg gtttaagaat tgtcaggctc ttcaaggatc aaggtacaag     480
gcgcacaagt cattttttggt cattgataat gtgatgactg atgatgcagg tgattatacc   540
```

```
tgtaaattta tacacaatga aaatggagcc aattatagtg tgacagcgac caggtccttc    600
acggtcaagg atgagcaagg cttctctctg tttcctgtaa tcagagcccc tgcacacaat    660
gaaacaaagg aagtggaaat tggagaaaac acaaacctaa cttgctctgc ttgttttgga    720
aaaggcgctc agttcttggc caccgtccag tggcagctta atggaaacaa aattacagac    780
ttcagtgaac caagaattca acaagaggaa gggcaaaatc aaagtttcag caatgggctg    840
gcttgtgtaa acacggtttt aagaatagct gatgtaaagg aagaggattt attgctgcgg    900
tacgactgtc tggccctgaa tttgcatggc ttgagaaggc acaccataag actaagtagg    960
aaaaatccaa ttgatcatca aagc                                           984
```

<210> SEQ ID NO 4
<211> LENGTH: 328
<212> TYPE: PRT
<213> ORGANISM: Macaca fascicularis

<400> SEQUENCE: 4

```
Met Gly Leu Trp Ile Leu Ala Ile Leu Thr Ile Leu Val Tyr Ser Thr
 1               5                  10                  15

Ala Ala Lys Phe Ser Lys Gln Ser Trp Gly Leu Glu Asn Glu Ala Leu
                20                  25                  30

Ile Val Arg Cys Pro Arg Gln Gly Lys Ser Ser Tyr Ile Val Asp Trp
            35                  40                  45

Tyr Tyr Ser Gln Thr Asn Lys Ser Ile Pro Thr Gln Glu Arg Asn Arg
        50                  55                  60

Val Phe Ala Ser Gly Gln Leu Leu Lys Phe Leu Pro Ala Glu Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Pro Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
130                 135                 140

Leu Glu Trp Phe Lys Asn Cys Gln Ala Leu Gln Gly Ser Arg Tyr Lys
145                 150                 155                 160

Ala His Lys Ser Phe Leu Val Ile Asp Asn Val Met Thr Asp Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Arg Ala Pro Ala His Asn Glu Thr Lys Glu
    210                 215                 220

Val Glu Ile Gly Glu Asn Thr Asn Leu Thr Cys Ser Ala Cys Phe Gly
225                 230                 235                 240

Lys Gly Ala Gln Phe Leu Ala Thr Val Gln Trp Gln Leu Asn Gly Asn
                245                 250                 255

Lys Ile Thr Asp Phe Ser Glu Pro Arg Ile Gln Gln Glu Glu Gly Gln
            260                 265                 270

Asn Gln Ser Phe Ser Asn Gly Leu Ala Cys Val Asn Thr Val Leu Arg
        275                 280                 285
```

```
Ile Ala Asp Val Lys Glu Glu Asp Leu Leu Leu Arg Tyr Asp Cys Leu
    290                 295                 300

Ala Leu Asn Leu His Gly Leu Arg Arg His Thr Ile Arg Leu Ser Arg
305                 310                 315                 320

Lys Asn Pro Ile Asp His Gln Ser
                325

<210> SEQ ID NO 5
<211> LENGTH: 1617
<212> TYPE: DNA
<213> ORGANISM: Macaca fascicularis

<400> SEQUENCE: 5
```

| | | | | | |
|---|---|---|---|---|---|
| aagtttagta | aacaatcgtg | gggcctggaa | aatgaggctt | taattgtgag | atgtcctaga | 60 |
| caaggaaaat | ctagttacat | cgtggattgg | tattactcac | aaacaaacaa | aagtattccc | 120 |
| acccaggaaa | gaaatcgtgt | gtttgcctca | ggccaacttc | ttaagtttct | accagctgaa | 180 |
| gttgctgatt | ctggtattta | tacctgcatt | gtcagaagtc | ccacattcaa | taggactgga | 240 |
| tatgcgaatg | tcaccatata | taaaaaacaa | ccagattgca | acgttccaga | ttatttgatg | 300 |
| tattcaaccg | tatctggatc | agaaaaaaat | tccaaaattt | actgtcctac | aattgacctc | 360 |
| tacaattgga | cagcacctct | tgagtggttt | aagaattgtc | aggctcttca | aggatcaagg | 420 |
| tacaaggcgc | acaagtcatt | tttggtcatt | gataatgtga | tgactgatga | tgcaggtgat | 480 |
| tatacctgta | aatttataca | caatgaaaat | ggagccaatt | atagtgtgac | agcgaccagg | 540 |
| tccttcacgg | tcaaggatga | gcaaggcttc | tctctgtttc | ctgtaatcag | agcccctgca | 600 |
| cacaatgaaa | caaggaagt | ggaaattgga | gaaaacacaa | acctaacttg | ctctgcttgt | 660 |
| tttggaaaag | gcgctcagtt | cttggccacc | gtccagtggc | agcttaatgg | aaacaaaatt | 720 |
| acagacttca | gtgaaccaag | aattcaacaa | gaggaagggc | aaaatcaaag | tttcagcaat | 780 |
| gggctggctt | gtgtaaacac | ggttttaaga | atagctgatg | taaaggaaga | ggatttattg | 840 |
| ctgcggtacg | actgtctggc | cctgaatttg | catggcttga | aaggcacac | cataagacta | 900 |
| agtaggaaaa | atccaattga | tcatcaaagc | acctactgca | taattgcagt | atgtagtgta | 960 |
| ttgttaatgc | taatcaatgt | cctggttatc | atcctaaaaa | cgttctggat | tgaggctact | 1020 |
| ctgctctgga | gggacatagc | taaaccttac | aagaccagga | tgatggaaa | gctctatgat | 1080 |
| gcttatgtta | tctacccacg | gaactacaca | tccagtacag | atggggccag | tcgtgtagag | 1140 |
| tactttgtcc | accagattct | gcccgatgtt | cttgaaaata | aatgtggcta | taccttatgc | 1200 |
| atttatggga | gagatatgct | acctggagaa | gatgtagtca | ctgcagtgga | aaccaacata | 1260 |
| cgaaagagca | ggcggcacat | tttcatcctg | accctcaga | tcacgcacaa | cgaggagttt | 1320 |
| gcctacgagc | aggaagttgc | cctgcatagt | gccctcatcc | agaacgactc | caaggtgatt | 1380 |
| cttattgaga | tggaggctct | gagcgagctg | gacatgctgc | aggctgaagc | gcttcaggac | 1440 |
| tctctcaggc | atctcatgga | agtgcagggc | accatcaagt | ggagggagga | ccacgttgcc | 1500 |
| aataaacggt | ccctgaattc | caaattctgg | aagcacgtga | ggtaccaaat | gcctgtgcca | 1560 |
| agcaaaatgc | ccagaaaggc | ctccagtttg | acttccttgg | cagcccagaa | gcagtag | 1617 |

```
<210> SEQ ID NO 6
<211> LENGTH: 538
<212> TYPE: PRT
<213> ORGANISM: Macaca fascicularis

<400> SEQUENCE: 6
```

-continued

```
Lys Phe Ser Lys Gln Ser Trp Gly Leu Glu Asn Glu Ala Leu Ile Val
 1               5                  10                  15

Arg Cys Pro Arg Gln Gly Lys Ser Ser Tyr Ile Val Asp Trp Tyr Tyr
                 20                  25                  30

Ser Gln Thr Asn Lys Ser Ile Pro Thr Gln Glu Arg Asn Arg Val Phe
             35                  40                  45

Ala Ser Gly Gln Leu Leu Lys Phe Leu Pro Ala Glu Val Ala Asp Ser
         50                  55                  60

Gly Ile Tyr Thr Cys Ile Val Arg Ser Pro Thr Phe Asn Arg Thr Gly
 65                  70                  75                  80

Tyr Ala Asn Val Thr Ile Tyr Lys Lys Gln Pro Asp Cys Asn Val Pro
                 85                  90                  95

Asp Tyr Leu Met Tyr Ser Thr Val Ser Gly Ser Glu Lys Asn Ser Lys
             100                 105                 110

Ile Tyr Cys Pro Thr Ile Asp Leu Tyr Asn Trp Thr Ala Pro Leu Glu
         115                 120                 125

Trp Phe Lys Asn Cys Gln Ala Leu Gln Gly Ser Arg Tyr Lys Ala His
     130                 135                 140

Lys Ser Phe Leu Val Ile Asp Asn Val Met Thr Asp Asp Ala Gly Asp
145                 150                 155                 160

Tyr Thr Cys Lys Phe Ile His Asn Glu Asn Gly Ala Asn Tyr Ser Val
                 165                 170                 175

Thr Ala Thr Arg Ser Phe Thr Val Lys Asp Glu Gln Gly Phe Ser Leu
             180                 185                 190

Phe Pro Val Ile Arg Ala Pro His Asn Glu Thr Lys Glu Val Glu
         195                 200                 205

Ile Gly Glu Asn Thr Asn Leu Thr Cys Ser Ala Cys Phe Gly Lys Gly
     210                 215                 220

Ala Gln Phe Leu Ala Thr Val Gln Trp Gln Leu Asn Gly Asn Lys Ile
225                 230                 235                 240

Thr Asp Phe Ser Glu Pro Arg Ile Gln Gln Glu Gly Gln Asn Gln
                 245                 250                 255

Ser Phe Ser Asn Gly Leu Ala Cys Val Asn Thr Val Leu Arg Ile Ala
             260                 265                 270

Asp Val Lys Glu Glu Asp Leu Leu Leu Arg Tyr Asp Cys Leu Ala Leu
         275                 280                 285

Asn Leu His Gly Leu Arg Arg His Thr Ile Arg Leu Ser Arg Lys Asn
     290                 295                 300

Pro Ile Asp His Gln Ser Thr Tyr Cys Ile Ile Ala Val Cys Ser Val
305                 310                 315                 320

Leu Leu Met Leu Ile Asn Val Leu Val Ile Ile Leu Lys Thr Phe Trp
                 325                 330                 335

Ile Glu Ala Thr Leu Leu Trp Arg Asp Ile Ala Lys Pro Tyr Lys Thr
             340                 345                 350

Arg Asn Asp Gly Lys Leu Tyr Asp Ala Tyr Val Ile Tyr Pro Arg Asn
         355                 360                 365

Tyr Thr Ser Ser Thr Asp Gly Ala Ser Arg Val Glu Tyr Phe Val His
     370                 375                 380

Gln Ile Leu Pro Asp Val Leu Glu Asn Lys Cys Gly Tyr Thr Leu Cys
385                 390                 395                 400

Ile Tyr Gly Arg Asp Met Leu Pro Gly Glu Asp Val Val Thr Ala Val
                 405                 410                 415

Glu Thr Asn Ile Arg Lys Ser Arg Arg His Ile Phe Ile Leu Thr Pro
```

```
                420             425             430
Gln Ile Thr His Asn Glu Glu Phe Ala Tyr Glu Gln Glu Val Ala Leu
            435             440             445
His Ser Ala Leu Ile Gln Asn Asp Ser Lys Val Ile Leu Ile Glu Met
        450             455             460
Glu Ala Leu Ser Glu Leu Asp Met Leu Gln Ala Glu Ala Leu Gln Asp
465             470             475             480
Ser Leu Arg His Leu Met Glu Val Gln Gly Thr Ile Lys Trp Arg Glu
                485             490             495
Asp His Val Ala Asn Lys Arg Ser Leu Asn Ser Lys Phe Trp Lys His
            500             505             510
Val Arg Tyr Gln Met Pro Val Pro Ser Lys Met Pro Arg Lys Ala Ser
        515             520             525
Ser Leu Thr Ser Leu Ala Ala Gln Lys Gln
530             535
```

<210> SEQ ID NO 7
<211> LENGTH: 1671
<212> TYPE: DNA
<213> ORGANISM: Macaca fascicularis

<400> SEQUENCE: 7

```
atgggctttt ggatcttagc aattctcaca attctcgtgt attccacagc agcgaagttt      60
agtaaacaat cgtggggcct ggaaaatgag gctttaattg tgagatgtcc tagacaagga     120
aaatctagtt acatcgtgga ttggtattac tcacaaacaa acaaaagtat tcccacccag     180
gaaagaaatc gtgtgtttgc ctcaggccaa cttcttaagt ttctaccagc tgaagttgct     240
gattctggta tttatacctg cattgtcaga agtcccacat tcaataggac tggatatgcg     300
aatgtcacca tatataaaaa acaaccagat tgcaacgttc cagattattt gatgtattca     360
accgtatctg gatcagaaaa aaattccaaa atttactgtc ctacaattga cctctacaat     420
tggacagcac ctcttgagtg gtttaagaat tgtcaggctc ttcaaggatc aagtacaag     480
gcgcacaagt cattttggt cattgataat gtgatgactg atgatgcagg tgattatacc     540
tgtaaattta tacacaatga aaatggagcc aattatagtg tgacagcgac caggtccttc     600
acggtcaagg atgagcaagg cttctctctg tttcctgtaa tcagaccccc tgcacacaat     660
gaaacaaagg aagtggaaat tggagaaaac acaaacctaa cttgctctgc ttgttttgga     720
aaaggcgctc agttcttggc caccgtccag tggcagctta atggaaacaa aattacagac     780
ttcagtgaac caagaattca acaagaggaa gggcaaaatc aaagtttcag caatgggctg     840
gcttgtgtaa acacggtttt aagaatagct gatgtaaagg aagaggattt attgctgcgg     900
tacgactgtc tggccctgaa tttgcatggc ttgagaaggc acaccataag actaagtagg     960
aaaaatccaa ttgatcatca agcacctac tgcataattg cagtatgtag tgtattgtta    1020
atgctaatca atgtcctggt tatcatccta aaaacgttct ggattgaggc tactctgctc    1080
tggagggaca tagctaaacc ttacaagacc aggaatgatg aaagctcta tgatgcttat    1140
gttatctacc cacggaacta cacatccagt acagatgggg ccagtcgtgt agagtacttt    1200
gtccaccaga ttctgcccga tgttcttgaa aataaatgtg ctatacctt atgcatttat    1260
gggagagata tgctacctgg agaagatgta gtcactgcag tggaaccaa catacgaaag    1320
agcaggcggc acattttcat cctgacccct cagatcacgc acaacgagga gtttgcctac    1380
gagcaggaag ttgccctgca tagtgccctc atccagaacg actccaaggt gattcttatt    1440
```

-continued

```
gagatggagg ctctgagcga gctggacatg ctgcaggctg aagcgcttca ggactctctc    1500
aggcatctca tggaagtgca gggcaccatc aagtggaggg aggaccacgt tgccaataaa    1560
cggtccctga attccaaatt ctggaagcac gtgaggtacc aaatgcctgt gccaagcaaa    1620
atgcccagaa aggcctccag tttgacttcc ttggcagccc agaagcagta g             1671
```

<210> SEQ ID NO 8
<211> LENGTH: 556
<212> TYPE: PRT
<213> ORGANISM: Macaca fascicularis

<400> SEQUENCE: 8

```
Met Gly Leu Trp Ile Leu Ala Ile Leu Thr Ile Leu Val Tyr Ser Thr
 1               5                  10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Ser Ser Tyr Ile Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Glu Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Pro Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Lys
145                 150                 155                 160

Ala His Lys Ser Phe Leu Val Ile Asp Asn Val Met Thr Asp Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Leu Phe Pro Val Ile Arg Ala Pro Ala His Asn Glu Thr Lys Glu
    210                 215                 220

Val Glu Ile Gly Glu Asn Thr Asn Leu Thr Cys Ser Ala Cys Phe Gly
225                 230                 235                 240

Lys Gly Ala Gln Phe Leu Ala Thr Val Gln Trp Gln Leu Asn Gly Asn
                245                 250                 255

Lys Ile Thr Asp Phe Ser Glu Pro Arg Ile Gln Gln Glu Glu Gly Gln
            260                 265                 270

Asn Gln Ser Phe Ser Asn Gly Leu Ala Cys Val Asn Thr Val Leu Arg
        275                 280                 285

Ile Ala Asp Val Lys Glu Glu Asp Leu Leu Leu Arg Tyr Asp Cys Leu
    290                 295                 300

Ala Leu Asn Leu His Gly Leu Arg Arg His Thr Ile Arg Leu Ser Arg
305                 310                 315                 320

Lys Asn Pro Ile Asp His Gln Ser Thr Tyr Cys Ile Ile Ala Val Cys
                325                 330                 335
```

-continued

```
Ser Val Leu Leu Met Leu Ile Asn Val Leu Ile Ile Leu Lys Thr
            340                 345                 350

Phe Trp Ile Glu Ala Thr Leu Leu Trp Arg Asp Ile Ala Lys Pro Tyr
        355                 360                 365

Lys Thr Arg Asn Asp Gly Lys Leu Tyr Asp Ala Tyr Val Ile Tyr Pro
370                 375                 380

Arg Asn Tyr Thr Ser Ser Thr Asp Gly Ala Ser Arg Val Glu Tyr Phe
385                 390                 395                 400

Val His Gln Ile Leu Pro Asp Val Leu Glu Asn Lys Cys Gly Tyr Thr
                405                 410                 415

Leu Cys Ile Tyr Gly Arg Asp Met Leu Pro Gly Glu Asp Val Val Thr
            420                 425                 430

Ala Val Glu Thr Asn Ile Arg Lys Ser Arg Arg His Ile Phe Ile Leu
        435                 440                 445

Thr Pro Gln Ile Thr His Asn Glu Glu Phe Ala Tyr Glu Gln Glu Val
    450                 455                 460

Ala Leu His Ser Ala Leu Ile Gln Asn Asp Ser Lys Val Ile Leu Ile
465                 470                 475                 480

Glu Met Glu Ala Leu Ser Glu Leu Asp Met Leu Gln Ala Glu Ala Leu
                485                 490                 495

Gln Asp Ser Leu Arg His Leu Met Glu Val Gln Gly Thr Ile Lys Trp
            500                 505                 510

Arg Glu Asp His Val Ala Asn Lys Arg Ser Leu Asn Ser Lys Phe Trp
        515                 520                 525

Lys His Val Arg Tyr Gln Met Pro Val Pro Ser Lys Met Pro Arg Lys
    530                 535                 540

Ala Ser Ser Leu Thr Ser Leu Ala Ala Gln Lys Gln
545                 550                 555
```

<210> SEQ ID NO 9
<211> LENGTH: 684
<212> TYPE: DNA
<213> ORGANISM: Homo sapiens

<400> SEQUENCE: 9

```
atgatggcgg ccggcgcggc cctagccctg gccttgtggc tactaatgcc accagtggag    60
gtgggagggg cggggccccc gccaatccag gacggtgagt tcacgttcct gttgccggcg   120
gggaggaagc agtgtttcta ccagtccgcg ccggccaacg caagcctcga gaccgaatac   180
caggtgatcg gaggtgctgg actggacgtg gacttcacgc tggagagccc tcagggcgtg   240
ctgttggtca gcgagtcccg caaggctgat ggggtacaca cggtggagcc aacggaggcc   300
ggggactaca agctgtgctt tgacaactcc ttcagcacca tctccgagaa gctggtgttc   360
tttgaactga tctttgacag cctccaggat gacgaggagg tcgaaggatg gcagaggct   420
gtggagcccg aggagatgct ggatgttaaa atggaggaca tcaaggagtc cattgagacc   480
atgcggaccc ggctggagcg cagcatccag atgctcacgc tactgcgggc cttcgaggca   540
cgtgaccgca acctgcaaga gggcaacttg gagcgggtca acttctggtc agctgtcaac   600
gtggcggtgc tgctgctggt ggctgtgctg caggtctgca cgctcaagcg cttcttccag   660
gacaagcgcc cggtgcccac gtag                                          684
```

<210> SEQ ID NO 10
<211> LENGTH: 556
<212> TYPE: PRT
<213> ORGANISM: Homo sapiens

<400> SEQUENCE: 10

```
Met Gly Phe Trp Ile Leu Ala Ile Leu Thr Ile Leu Met Tyr Ser Thr
 1               5                  10                  15
Ala Ala Lys Phe Ser Lys Gln Ser Trp Gly Leu Glu Asn Glu Ala Leu
            20                  25                  30
Ile Val Arg Cys Pro Arg Gln Gly Lys Pro Ser Tyr Thr Val Asp Trp
        35                  40                  45
Tyr Tyr Ser Gln Thr Asn Lys Ser Ile Pro Thr Gln Glu Arg Asn Arg
    50                  55                  60
Val Phe Ala Ser Gly Gln Leu Leu Lys Phe Leu Pro Ala Ala Val Ala
65                  70                  75                  80
Asp Ser Gly Ile Tyr Thr Cys Ile Val Arg Ser Pro Thr Phe Asn Arg
                85                  90                  95
Thr Gly Tyr Ala Asn Val Thr Ile Tyr Lys Lys Gln Ser Asp Cys Asn
            100                 105                 110
Val Pro Asp Tyr Leu Met Tyr Ser Thr Val Ser Gly Ser Glu Lys Asn
        115                 120                 125
Ser Lys Ile Tyr Cys Pro Thr Ile Asp Leu Tyr Asn Trp Thr Ala Pro
    130                 135                 140
Leu Glu Trp Phe Lys Asn Cys Gln Ala Leu Gln Gly Ser Arg Tyr Arg
145                 150                 155                 160
Ala His Lys Ser Phe Leu Val Ile Asp Asn Val Met Thr Glu Asp Ala
                165                 170                 175
Gly Asp Tyr Thr Cys Lys Phe Ile His Asn Glu Asn Gly Ala Asn Tyr
            180                 185                 190
Ser Val Thr Ala Thr Arg Ser Phe Thr Val Lys Asp Glu Gln Gly Phe
        195                 200                 205
Ser Leu Phe Pro Val Ile Gly Ala Pro Ala Gln Asn Glu Ile Lys Glu
    210                 215                 220
Val Glu Ile Gly Lys Asn Ala Asn Leu Thr Cys Ser Ala Cys Phe Gly
225                 230                 235                 240
Lys Gly Thr Gln Phe Leu Ala Ala Val Leu Trp Gln Leu Asn Gly Thr
                245                 250                 255
Lys Ile Thr Asp Phe Gly Glu Pro Arg Ile Gln Gln Glu Glu Gly Gln
            260                 265                 270
Asn Gln Ser Phe Ser Asn Gly Leu Ala Cys Leu Asp Met Val Leu Arg
        275                 280                 285
Ile Ala Asp Val Lys Glu Glu Asp Leu Leu Leu Gln Tyr Asp Cys Leu
    290                 295                 300
Ala Leu Asn Leu His Gly Leu Arg Arg His Thr Val Arg Leu Ser Arg
305                 310                 315                 320
Lys Asn Pro Ile Asp His His Ser Ile Tyr Cys Ile Ile Ala Val Cys
                325                 330                 335
Ser Val Phe Leu Met Leu Ile Asn Val Leu Val Ile Ile Leu Lys Met
            340                 345                 350
Phe Trp Ile Glu Ala Thr Leu Leu Trp Arg Asp Ile Ala Lys Pro Tyr
        355                 360                 365
Lys Thr Arg Asn Asp Gly Lys Leu Tyr Asp Ala Tyr Val Val Tyr Pro
    370                 375                 380
Arg Asn Tyr Lys Ser Ser Thr Asp Gly Ala Ser Arg Val Glu His Phe
385                 390                 395                 400
Val His Gln Ile Leu Pro Asp Val Leu Glu Asn Lys Cys Gly Tyr Thr
```

```
                    405                 410                 415
Leu Cys Ile Tyr Gly Arg Asp Met Leu Pro Gly Glu Asp Val Val Thr
            420                 425                 430
Ala Val Glu Thr Asn Ile Arg Lys Ser Arg Arg His Ile Phe Ile Leu
        435                 440                 445
Thr Pro Gln Ile Thr His Asn Lys Glu Phe Ala Tyr Glu Gln Glu Val
    450                 455                 460
Ala Leu His Cys Ala Leu Ile Gln Asn Asp Ala Lys Val Ile Leu Ile
465                 470                 475                 480
Glu Met Glu Ala Leu Ser Glu Leu Asp Met Leu Gln Ala Glu Ala Leu
                485                 490                 495
Gln Asp Ser Leu Gln His Leu Met Lys Val Gln Gly Thr Ile Lys Trp
            500                 505                 510
Arg Glu Asp His Ile Ala Asn Lys Arg Ser Leu Asn Ser Lys Phe Trp
        515                 520                 525
Lys His Val Arg Tyr Gln Met Pro Val Pro Ser Lys Ile Pro Arg Lys
    530                 535                 540
Ala Ser Ser Leu Thr Pro Leu Ala Ala Gln Lys Gln
545                 550                 555

<210> SEQ ID NO 11
<211> LENGTH: 23
<212> TYPE: DNA
<213> ORGANISM: Artificial Sequence
<220> FEATURE:
<223> OTHER INFORMATION: Human Oligos used for RT-PCR of cyno ST2L

<400> SEQUENCE: 11
agatataggc tactcttccc aac                                           23

<210> SEQ ID NO 12
<211> LENGTH: 21
<212> TYPE: DNA
<213> ORGANISM: Artificial Sequence
<220> FEATURE:
<223> OTHER INFORMATION: Human Oligos used for RT-PCR of cyno ST2L

<400> SEQUENCE: 12
ctcctcacac ttcagtgcag g                                             21

<210> SEQ ID NO 13
<211> LENGTH: 20
<212> TYPE: DNA
<213> ORGANISM: Artificial Sequence
<220> FEATURE:
<223> OTHER INFORMATION: T3 primer

<400> SEQUENCE: 13
aattaaccct cactaaaggg                                               20

<210> SEQ ID NO 14
<211> LENGTH: 20
<212> TYPE: DNA
<213> ORGANISM: Artificial Sequence
<220> FEATURE:
<223> OTHER INFORMATION: T7 primer

<400> SEQUENCE: 14
taatacgact cactataggg                                               20

<210> SEQ ID NO 15
```

```
<211> LENGTH: 37
<212> TYPE: DNA
<213> ORGANISM: Artificial Sequence
<220> FEATURE:
<223> OTHER INFORMATION: Cyno Oligos with NotI site

<400> SEQUENCE: 15
gtagcagcgg ccgccaccat ggggctttgg atcttag                    37

<210> SEQ ID NO 16
<211> LENGTH: 30
<212> TYPE: DNA
<213> ORGANISM: Artificial Sequence
<220> FEATURE:
<223> OTHER INFORMATION: Cyno Oligo with BamHI site

<400> SEQUENCE: 16
tgctacggat ccctactgct tctgggctgc                            30
```